United States Patent [19]

Kordes

[11] Plant 4,672

[45] Mar. 17, 1981

[54] ROSE PLANT

[75] Inventor: Reimer Kordes, Aspern, Fed. Rep. of Germany

[73] Assignee: Armstrong Nurseries, Inc., Ontario, Calif.

[21] Appl. No.: 105,782

[22] Filed: Dec. 19, 1979

[51] Int. Cl.[3] ..... A01H 5/00

[52] U.S. Cl. ..... Plt./27

[58] Field of Search ..... Plt./27

*Primary Examiner*—James R. Feyrer

*Attorney, Agent, or Firm*—William H. Elliott, Jr.; Andrew R. Klein

[57] ABSTRACT

A new variety of rose plant of the hybrid Floribunda class, being a hardy outdoor seedling of the bush type, well adapted for mass display because its blooms are abundant, most of them being carried in clusters of as many as five or more to a stem. Flowers are from 2½ to 3½ inches across, and have from 32 to 40 petals and from 0 to 5 petaloids. The flower coloration is a distinctive purple-red as hereinafter described in detail.

1 Drawing Figure

This invention relates to a new variety of hybrid Floribunda rose. The plant is a hardy bushy outdoor seedling grown mainly for garden decoration. It was hybridized and asexually reproduced by Reimer Kordes in Sparrieshoop, Holstein, West Germany, having as its seed parent "Zorina" (Plant Pat. No. 2,321) and for pollen parent "Silver Star". The plants described herein have been asexually reproduced by budding in Ontario, Calif., from budwood of the new variety. The new variety holds its distinguishing characteristics through succeeding propagations by budding.

The plant bears its flowers usually three to five or more in irregular rounded clusters, on strong medium to long stems. It blooms freely to abundantly outdoors, and nearly continuously during the growing season. The blooms have a slight tea fragrance.

This rose cultivar may most readily be distinguished from its seed parent, Zorina, by the following combination of characteristics:

Whereas Zorina bears buds and flowers of grenadine-red coloration, the new rose bears buds and flowers of a purple-red coloration essentially as more fully described below, and as illustrated herein.

The new cultivar bears flowers with significantly greater petalage (from 32 to 40) than Zorina, which bears flowers with about 25 petals.

Zorina was designated as a cultivar for greenhouse cut flower usage, whereas the new rose is strictly for garden decoration.

This new rose cultivar may be distinguished from its pollen parent, Silver Star, by the following combination of characteristics:

Whereas the new cultivar bears buds and flowers of a purple-red coloration, Silver Star bears buds and flowers of a light lavender coloration.

Silver Star has large open flowers of 5 inch diameter, whereas the new cultivar has significantly smaller open flowers of 2½ to 3½ inch diameter.

Whereas Silver Star is classified as a hybrid Tea rose, the new cultivar is classified as a hybrid Floribunda.

The accompanying drawing illustrates the plant in color, and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is average length to long and of average caliper, erect and stiff, almost smooth, but with some stipitate glands. The color is between Moderate Yellow Green, 5GY5/6, and Moderate Yellow Green, 2.5GY5/5.

Before the calyx breaks, the bud is medium in size, for Floribunda roses, of medium length, ovoid, with a few stipitate glands on the surface of the bud. There are usually slender foliaceous parts extending beyond the tip of the bud equal to one-fourth or more of its length.

As the calyx breaks, the color is between Dark Red, 2.5R3/7, and Deep Purplish Red, 10RP3/10. The inner surface of the sepals carries a fine tomentum. Margins are lined with stipitate glands.

As the first petal opens, the bud is of average size for Floribunda roses, of medium length and ovoid. The color on the outside of the petal is between Moderate Red, 2.5R4/10, and Strong Purplish Red, 10RP4/12. The color on the inside of the petal is between Moderate Red, 2.5R4/10, and Strong Purplish Red, 7.5RP4/11. At the basal attachment zone on both the outside and inside of the petal, the color is between white and Brilliant Yellow Green, 2.5GY9/8. The bud opens up well and is not prevented from opening by cold, hot, wet or dry weather.

BLOOM

When fully open, the bloom is average size for Floribunda roses, being from 2½ to 3½ inches in diameter. The petalage is double, with from 32 to 40 petals, plus from 0 to 5 petaloids arranged regularly. In form, the bloom is cupped at first, the petals remaining at first somewhat cupped with tips reflexed outward, becoming later at maturity more loosely cupped, with tips reflexed outward.

The petals are of medium thickness, with inside slightly satiny and outside shiny to satiny. The outside petals are broadly obovate, with apex flat. Intermediate petals are also broadly obovate, but with apex rounded. Inside petals are obovate with mucronate apex. The colors may be modified by being shaded and/or washed or tinted with other colors.

The description which follows is of the color values noted in a flower newly opened in the month of June. The plant had been grown outdoors in Ontario, Calif.

All petals, outside, intermediate and inside, were of the same coloration. The basal attachment zone was between white and Brilliant Yellow Green, 5GY9/8. The remainder of the outer surface was between Deep Purplish Pink, 7.5RP6/12, and Strong Purplish Red, 7.5RP4/11, while the remainder of the inner surface was between Deep Purplish Pink, 5RP6/10, and Strong Purplish Red, 7.5RP4/11.

The following description is of a rose that was open for three days. It had been grown outdoors in the month of June, in Ontario, Calif.

All petals, outside and inside, were of the same coloration. The basal attachment zone outside and inside was between white and Brilliant Yellow Green, 5GY9/8. The remainder of the outer surface was near Deep Purplish Pink, 5RP6/10, while the remainder of the inner surface was between Deep Purplish Pink, 5RP6/10, and Moderate Purplish Red, 5RP5/10.

The general color effect of the newly opened flower is between Deep Purplish Pink, 5RP6/10, and Strong Purplish Red, 7.5RP4/11. After being three days open, the bloom gives a general color effect of between Deep Purplish Pink, 5RP6/10, and Moderate Purplish Red, 5RP5/10. The petals drop off cleanly, and are not particularly affected by cold, hot, wet or dry weather.

The flower on the bush in the garden persists for from 4 to 5 days in the month of June, in the locality named. Cut roses grown outdoors and kept at living-room temperatures will last from 3 to 4 days in the month of July.

REPRODUCTIVE ORGANS

There are many stamens, arranged regularly about the pistils.

The filaments are medium-length and near Brilliant Yellow, 5Y9/9, in color. Most are with anthers.

Anthers are medium in size, all opening approximately at once. The color, just prior to dehiscense, is near Moderate Orange Yellow, 10YR8/10.

There is a moderate amount of pollen, which is near Brilliant Yellow, 5Y9/9, in coloration.

There are many pistils, approximately 70 in number.

The styles are moderately uneven, long and of average caliper and loosely bunched. The coloration is near Strong Purplish Red, 10RP4/12.

The color of the stigma is near Brilliant Greenish Yellow, 7.5Y9/8.

Most of the ovaries are enclosed in the calyx.

Immature hips are of average length, ovoid and near Strong Yellow Green, 5GY6/8, in color.

The sepals are permanent. They are medium-length, straight and, on the inside, are near Moderate Yellow Green, 5GY5/6, in color, with a heavy gray bloom. The outside of the sepals is between Moderate Yellow Green, 5GY5/6, and Moderate Yellow Green, 2.5GY5/5, in color.

There are an average number of seeds, from 3 to 12 in number, and small to medium-size.

FOLIAGE

The compound leaves usually comprise from three to seven leaflets. They are from normal to abundant, of medium size to large, moderately heavy to somewhat leathery, and glossy. The leaflets are ovate in form, with apex acute, base obtuse, and margin doubly serrate.

On its upper surface, the mature foliage is between Dark Yellowish Green, 2.5G3/3, and Grayish Olive Green, 7.5GY3/2, in color. The under surface is between gray and Moderate Yellow Green, 2.5GY5/5.

The upper surface of the young foliage is near Dark Red, 2.5R3/7, in color, while the under surface shows a coloration which is between Dark Red, 2.5R3/7, and Moderate Red, 2,5R4/10.

The rachis is of average size, the upper side being grooved, with a few stipitate glands on the edges. The under side is moderately prickly.

The stipules are medium-length, medium-width, and with medium-length points turning out at an angle of more than 45°.

The plant displays a more than average resistance to mildew, when compared to other varieties now in commerce grown under comparable conditions.

GROWTH

The plant is upright and bushy in habit and much branched. It displays a very vigorous growth. Canes are of medium to heavy caliper.

The main stems are between Light Olive, 10Y5/5, and Moderate Yellow Green, 2.5GY5/5, in coloration. They bear very few large prickles, which are medium-length and hooked slightly downward, with a medium-length, moderately narrow base. Their color is between gray and Moderate Yellowish Brown, 10YR4/4. There are no small prickles and no hairs.

The branches are between Moderate Yellow Green, 2.5GY5/5, and Moderate Olive Green, 5GY4/3, in coloration. They carry very few large prickles, which are medium-length and hooked slightly downward, with a medium-length, moderately narrow base. They are near Brownish Orange, 2.5YR5/9, in color. There are no small prickles and no hairs.

New shoots are near Dark Red, 2.5R3/7, in coloration. They bear very few medium-length large prickles, which are hooked slightly downward, with a medium-length, moderately narrow base. They are near Dark Red, 2.5R3/7, in color. There are no small prickles and no hairs.

I claim:

1. A new and distinct variety of Floribunda rose plant, substantially as herein shown and described, and being especially characterized in the distinctive purple-red coloration of its blooms, and in the abundance of its dark green glossy foliage, which covers the plant during the growing season.

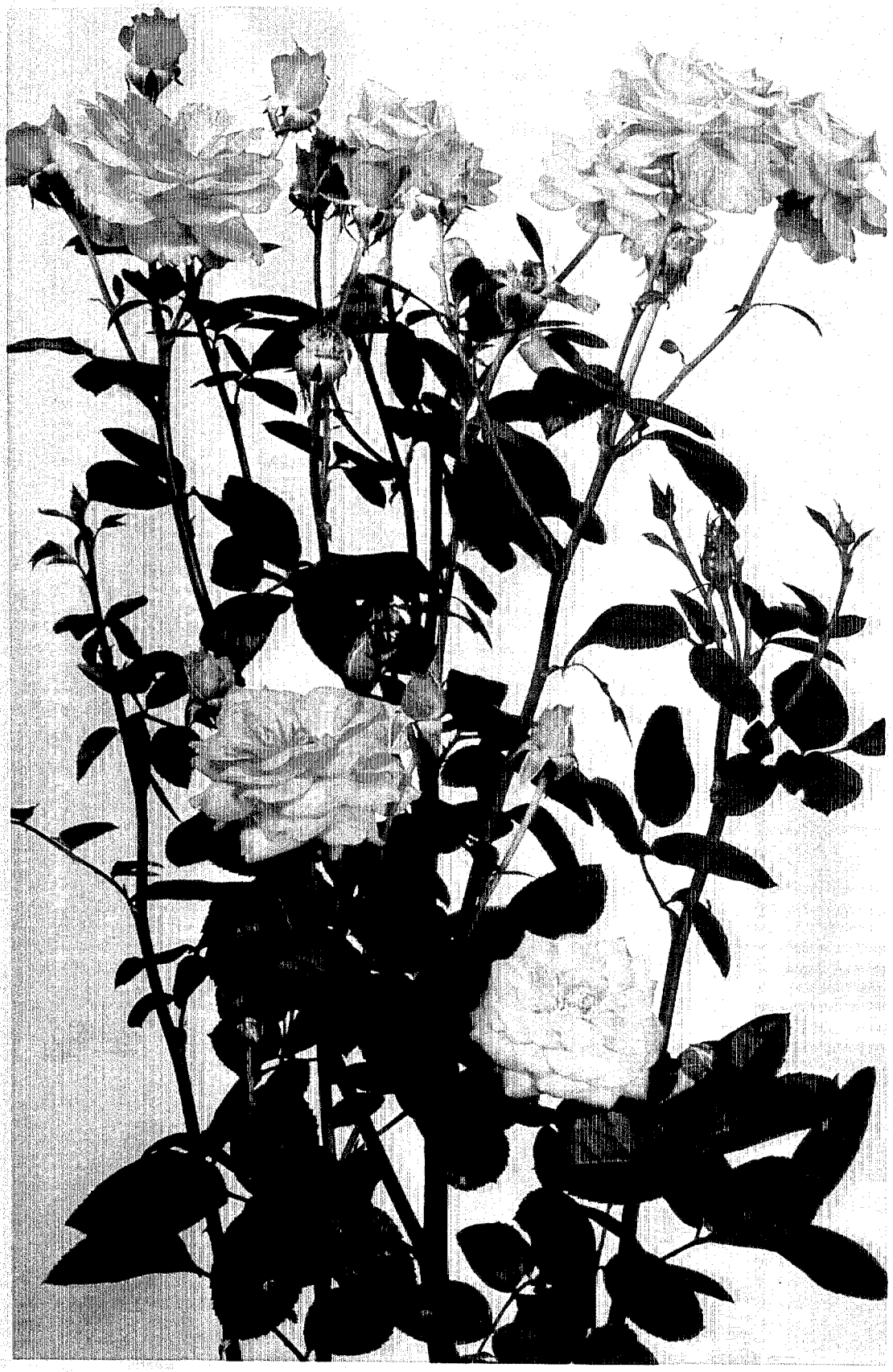

* * * * *